United States Patent
Ikeda et al.

(10) Patent No.: US 11,470,858 B2
(45) Date of Patent: Oct. 18, 2022

(54) METHOD FOR PRODUCING LACTOFERRIN-CONTAINING AQUEOUS SOLUTION

(71) Applicant: MORINAGA MILK INDUSTRY CO., LTD., Tokyo (JP)

(72) Inventors: Masayuki Ikeda, Kanagawa (JP); Junichi Hashimoto, Kanagawa (JP); Ichizou Shinoda, Kanagawa (JP); Hiroshi Iwamoto, Kanagawa (JP); Yasuhiro Takeda, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/970,224

(22) PCT Filed: Jan. 8, 2019

(86) PCT No.: PCT/JP2019/000245
§ 371 (c)(1),
(2) Date: Aug. 14, 2020

(87) PCT Pub. No.: WO2019/176246
PCT Pub. Date: Sep. 19, 2019

(65) Prior Publication Data
US 2021/0137136 A1 May 13, 2021

(30) Foreign Application Priority Data

Mar. 12, 2018 (JP) .............................. JP2018-044770

(51) Int. Cl.
*A23J 3/08* (2006.01)
*A23J 1/20* (2006.01)

(52) U.S. Cl.
CPC .. *A23J 3/08* (2013.01); *A23J 1/20* (2013.01)

(58) Field of Classification Search
CPC ...................................... A23J 3/08; A23J 1/20
(Continued)

(56) References Cited

U.S. PATENT DOCUMENTS

| 4,668,771 | A  | * | 5/1987 | Kawakami | ............. | C07K 14/79 |
|           |    |   |        |          |              | 530/366 |
| 2016/0044949 | A1 | * | 2/2016 | Urazono | ................. | A61P 37/02 |
|           |    |   |        |          |              | 424/94.4 |

FOREIGN PATENT DOCUMENTS

| EP | 0364912 A2 | * | 4/1990 | ................ A23J 3/08 |
| EP | 0364912 A2 |   | 4/1990 |                            |

(Continued)

OTHER PUBLICATIONS

International Search Report for PCT Patent App. No. PCT/JP2019/000245 (dated Mar. 12, 2019).

(Continued)

*Primary Examiner* — Brent T O'Hern
(74) *Attorney, Agent, or Firm* — Cermak Nakajima & McGowan LLP; Shelly Guest Cermak

(57) ABSTRACT

There is provided a means for sterilizing lactoferrin at a high temperature in a short time while maintaining the activity of the lactoferrin. The present technology provides a method for producing a lactoferrin-containing aqueous solution, including a sterilization step of heat-sterilizing a lactoferrin-containing aqueous solution, in which the total mass content of proteins other than lactoferrin is $\frac{1}{12}$ or less of the mass content of lactoferrin, at a temperature of 100° C. or more. The present technology also provides a lactoferrin-containing aqueous solution in which the total mass content of proteins other than lactoferrin is $\frac{1}{12}$ or less of the mass content of lactoferrin, and which does not contain living bacteria.

8 Claims, 5 Drawing Sheets

(58) Field of Classification Search
USPC .......................................................... 426/657
See application file for complete search history.

(56) References Cited

FOREIGN PATENT DOCUMENTS

| | | |
|---|---|---|
| EP | 0437958 A1 | 7/1991 |
| EP | 2258380 A1 | 12/2010 |
| EP | 2984935 A1 | 2/2016 |
| JP | 2-108629 A | 4/1990 |
| JP | 02-108630 A | 4/1990 |
| JP | 3-215500 A | 9/1991 |
| JP | 8-98655 A | 4/1996 |
| JP | 2000-210014 A | 8/2000 |
| JP | 2000-287657 A | 10/2000 |
| JP | 2006-187300 A | 7/2006 |
| JP | 2010-180219 A | 8/2010 |
| JP | 2014-193125 A | 10/2014 |
| WO | WO2009/122719 A1 | 10/2009 |

OTHER PUBLICATIONS

Extended European Search Report for European Patent App. No. 19766586.2 (dated Nov. 11, 2021).

* cited by examiner

METHOD FOR PRODUCING LACTOFERRIN-CONTAINING AQUEOUS SOLUTION

This application is a national phase entry under 35 U.S.C. § 371 of PCT Patent Application No. PCT/JP2019/000245, filed on Jan. 8, 2019, which claims priority under 35 U.S.C. § 119 to Japanese Patent Application No. 2018-044770, filed Mar. 12, 2018, both of which are incorporated by reference.

TECHNICAL FIELD

The present technology relates to a method for producing a lactoferrin-containing aqueous solution, and more particularly to a method for producing a lactoferrin-containing aqueous solution, including a sterilization step.

BACKGROUND ART

Sterilization of a food product is performed in order to ensure the preservability and safety of the food product. For many food products, killing microorganisms by heating is performed for sterilization. Also for lactoferrin, which is a food material that has recently received attention, some methods have been proposed for heat-sterilizing lactoferrin while maintaining its activity.

For example, the below-listed patent literature discloses a method which involves heat-sterilizing an aqueous lactoferrin solution after adjusting the ionic strength of the aqueous solution so that it satisfies a predetermined formula. The below-listed patent literature 2 discloses a method which involves adjusting the pH of a lactoferrin-containing liquid to be 1.0 or more and 6.5 or less, and heating the liquid at a temperature of 60° C. or more.

The below-listed patent literature 3 discloses a thermally stable lactoferrin composition composed of a lactoferrin and at least one stabilizer selected from a glycerin fatty acid ester, casein sodium, and lecithin. The patent literature 3 teaches that the composition can be heated at a temperature of 90° C. or more without deactivating the lactoferrin. The below-listed patent literature 4 discloses a thermally stable protein composition composed of a milk basic protein fraction and at least one stabilizer selected from a soybean polysaccharide, xanthane gum, pectin, gum arabic, ghatti gum, carrageenan, locust bean gum, casein sodium, lecithin, and carboxymethyl cellulose. The patent literature 4 teaches that the composition can be heated at a temperature of 90° C. or more without deactivating the milk basic protein fraction.

CITATION LIST

Patent Literature

Patent literature 1: Japanese Patent Laid-Open Publication No. H2-108629
Patent literature 2: Japanese Patent Laid-Open Publication No. H3-215500
Patent literature 3: Japanese Patent Laid-Open Publication No. 2010-180219
Patent literature 4: Japanese Patent Laid-Open Publication No. 2014-193125

SUMMARY OF INVENTION

Technical Problem

Some bacteria to be sterilized are hard to kill. For example, sporulating bacteria are hard to kill. In order to sterilize hard-to-kill bacteria, a high sterilization temperature is sometimes employed in heat sterilization of the bacteria. Such heat sterilization methods may include ultra-high temperature heat treatment (UHT) (heat treatment at 120 to 150° C. for 1 to 5 seconds) and high-temperature short-time sterilization (HTST) (heat treatment at 72 to 75° C. for 15 seconds). When it is not possible to employ a high sterilization temperature, a method may be employed which employs, for example, a low temperature and a prolonged heating time. Such a low-temperature sterilization method can be exemplified by low-temperature long-time sterilization (LTLT) (heat treatment at 62 to 65° C. for 30 minutes).

Sterilization conditions to be employed may vary depending on a type of a food product. Sterilization at a particularly high temperature is required for the production of a food product capable of long-term storage and room-temperature distribution. For example, in order to kill a spore of *Clostridium botulinum*, which is known as a bacterium that causes food poisoning, sterilization conditions of a heating temperature of 120° C. and a heating time of 4 minutes or more are required for the sterilization of a retort food product which is capable of long-term storage. The UHT method is a mainstream technology for the heat sterilization of a liquid food product such as a soft drink, a milk beverage, or mineral water.

It will be very useful in using lactoferrin as a food material if lactoferrin can be sterilized at a high temperature in a short time while maintaining the activity of the lactoferrin.

As described above, there are some disclosed methods for sterilizing lactoferrin. However, in order to employ a sterilization temperature of 120° C. or more in the method described in the above-listed patent literature 1, it is theoretically necessary to make the ionic strength 0.1 μM or less with salt. When the method described in the above-listed patent literature 2 is used, the activity of lactoferrin cannot be maintained if it is sterilized at a high temperature of 120° C. or more. Each of the compositions of the above-listed patent literatures 3 and 4 contains the stabilizer. The stabilizer will change the flavor and/or the physical properties and, in addition, may increase the cost.

A demand therefore exists for a new method to sterilize lactoferrin at a high temperature in a short time while maintaining the activity of the lactoferrin.

Solution to Problem

The present inventors have found a new method to sterilize lactoferrin at a high temperature in a short time while maintaining the activity of the lactoferrin.

Thus, the present technology provides the following:

[1] A method for producing a lactoferrin-containing aqueous solution, comprising a sterilization step of heat-sterilizing a lactoferrin-containing aqueous solution, in which the total mass content of proteins other than lactoferrin is 1/12 or less of the mass content of lactoferrin, at a temperature of 100° C. or more.

[2] The method as described in [1], wherein the salt concentration of the lactoferrin-containing aqueous solution to be subjected to the sterilization step is 5 mM or less.

[3] The method as described in [1] or [2], wherein the lactoferrin concentration of the lactoferrin-containing aqueous solution to be subjected to the sterilization step is 400 mg/ml or less.

[4] The method as described in any one of [1] to [3], wherein a heat sterilization temperature in the sterilization step is 120° C. or more.

[5] The method as described in any one of [1] to [4], wherein the heat sterilization temperature and time in the sterilization step are 120° C. or more and 4 minutes or more, respectively.

[6] The method as described in any one of [1] to [5], wherein the lactoferrin-containing aqueous solution to be subjected to the sterilization step does not contain a stabilizer.

[7] The method as described in any one of [1] to [6], wherein the COMT inhibitory activity of lactoferrin in the lactoferrin-containing aqueous solution to be subjected to the sterilization step is maintained at a level of 80% or more after the sterilization step.

The present technology also provides the following:

[8] A lactoferrin-containing aqueous solution in which the total mass content of proteins other than lactoferrin is $1/12$ or less of the mass content of lactoferrin, and which does not contain living bacteria.

[9] The lactoferrin-containing aqueous solution as described in [8], having a salt concentration of 5 mM or less.

[10] The lactoferrin-containing aqueous solution as described in [8] or [9], having a lactoferrin concentration of 400 mg/ml or less.

[11] The lactoferrin-containing aqueous solution as described in any one of [8] to [10], not containing a stabilizer.

Advantageous Effects of Invention

According to the present technology, it is possible to sterilize lactoferrin at a high temperature in a short time while maintaining the activity of the lactoferrin.

The effects of the present technology are not limited to such effects, and may also include those effects as described in the present specification.

DESCRIPTION OF EMBODIMENTS

Figure 1:
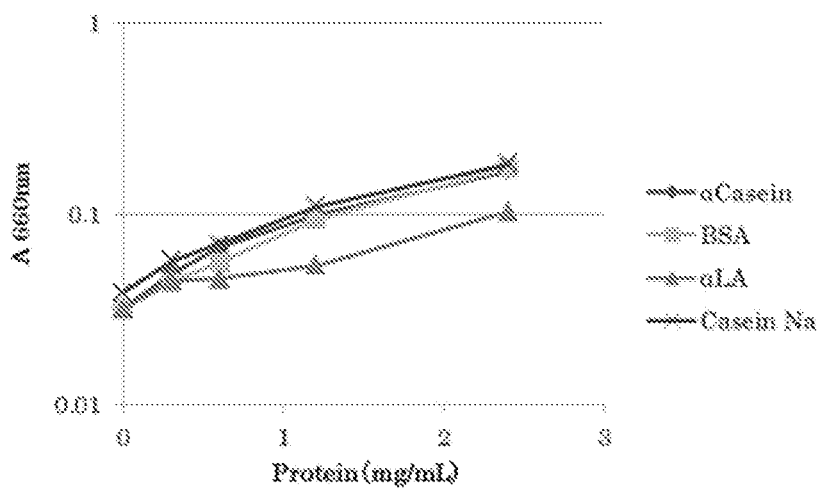
FIG. 1 is a graph showing the results of measurement of the turbidities of lactoferrin-containing aqueous solutions after autoclave sterilization.

Preferred embodiments of the present technology will now be described. The present technology is not intended to be limited to the preferred embodiments, and can be arbitrarily modified within the scope of the present technology.

1. Method for Producing Lactoferrin-Containing Aqueous Solution (1) Sterilization Step The production method according to the present technology includes a sterilization step of heat-sterilizing a lactoferrin-containing aqueous solution, in which the total mass content of proteins other than lactoferrin is $1/12$ or less of the mass content of lactoferrin, at a temperature of 100° C. or more. The sterilization step can sterilize lactoferrin at a high temperature in a short time while maintaining the activity of the lactoferrin.

Lactoferrin is an iron-binding glycoprotein that exists in body fluids such as milk, tears, saliva and blood. Lactoferrin is contained in the milk of a mammal such as sheep, goat, pig, mouse, buffalo, camel, yak, horse, donkey, llama, cow or human.

Lactoferrin for use in the present technology may be derived from the milk of a mammal. From the viewpoint of lactoferrin content and availability, cow milk or human milk, for example, is preferred as a source for obtaining lactoferrin, and cow milk is especially preferred as a source for obtaining lactoferrin. Thus, lactoferrin derived e.g. from cow milk or human milk, preferably from cow milk may be used in the present technology. Any of colostrum, transitional milk, normal milk and late lactation milk can be used. A commercially available lactoferrin may be used in the present technology.

Lactoferrin for use in the present technology may be one which has been isolated by a common method (e.g. ion chromatography) from skim milk or whey obtained by processing the milk of a mammal.

Lactoferrin for use in the present technology may be either glycosylated or non-glycosylated.

Lactoferrin commonly used in the field of foods and beverages is milk-derived (in particular cow milk-derived) lactoferrin. In many cases, milk-derived lactoferrin is obtained from whey. Milk-derived lactoferrin, obtained in such a manner, contains proteins other than lactoferrin. Thus, what is commonly used as lactoferrin in the field of foods and drinks is a composition comprising lactoferrin and proteins other than lactoferrin.

The present inventors have found that lactoferrin can be sterilized at a high temperature in a short time while maintaining the activity of the lactoferrin by decreasing the content of proteins other than lactoferrin in a lactoferrin-containing aqueous solution to be subjected to heat sterilization.

It appears that the use of a temperature of 100° C. or more is not envisaged in the above-listed patent literatures and 2 which disclose the above-described lactoferrin sterilization methods. The techniques described in the above-listed patent literatures 3 and 4, which envisage the use of a temperature of 100° C. or more, assume the use of a stabilizer to enhance the heat resistance of lactoferrin. According to the present technology, it becomes possible, even without using such a stabilizer, to use a high temperature of 100° C. or more, in particular a high temperature of 120° C. or more, for sterilization of lactoferrin by decreasing the content of contaminating proteins other than lactoferrin in a lactoferrin-containing aqueous solution.

The total mass content of proteins other than lactoferrin is $1/12$ or less of the mass content of lactoferrin in a lactoferrin-containing aqueous solution to be subjected to the sterilization step. By thus adjusting the total mass content of proteins other than lactoferrin, the lactoferrin does not form a precipitate and can maintain its activity even though it is heated at a temperature of 100° C. or more.

In the present invention, the proteins may include milk-derived proteins such as casein and whey, microorganisms that contaminate lactoferrin during a lactoferrin purification process, protein impurities flying in the air, proteins from bovine blood, etc. When the lactoferrin is produced as a recombination protein by *Escherichia coli*, the proteins other than lactoferrin may include a protein(s) from a culture medium component.

In a lactoferrin-containing aqueous solution to be subjected to the sterilization step, the total mass content of proteins other than lactoferrin is 1/12 or less, preferably 1/14 or less, more preferably 1/16 or less, even more preferably 1/18 or less, and particularly preferably 1/20 or less of the mass content of lactoferrin. By thus further reducing the total mass content of proteins other than lactoferrin, the formation of a precipitate is less likely to occur and the activity of lactoferrin is better maintained when the aqueous solution is heated at a temperature of 100° C. or more, particularly at a temperature of 120° C. or more.

The total mass content of proteins other than lactoferrin and the mass content of lactoferrin can be measured by performing HPLC separation. In particular, a lactoferrin-containing aqueous solution is subjected to reversed-phase HPLC separation using Alliance e2695 (manufacture by Waters Corporation). Next, a fraction having an absorption peak at 280 nm is separated into a fraction containing lactoferrin and a fraction containing proteins other than lactoferrin. The inclusion of lactoferrin in a fraction can be checked, for example, by using a commercially available antibody against lactoferrin. The former fraction and the latter fraction are each collected. A solvent is removed from each fraction by freeze-drying, and the freeze-dried product of each fraction is dissolved in newly-added water. The amount of the protein contained in each of the former fraction and the latter fraction is measured by protein assay using a dye method. The content of lactoferrin and the content of proteins other than lactoferrin can be measured in this manner.

In a lactoferrin-containing aqueous solution to be subjected to the sterilization step, the lower limit of the total mass content of proteins other than lactoferrin may be, for example, 0% by mass or, from the viewpoint of the production efficiency of a lactoferrin material to be used for the preparation of the aqueous solution, may be more than 0% by mass. Thus, in a lactoferrin-containing aqueous solution to be subjected to the sterilization step, the total mass content of proteins other than lactoferrin may be, for example, 1/100,000 or more, 1/10,000 or more, 1/5,000 or more, 1/1,000 or more, or 1/100 or more.

The heat sterilization temperature in the sterilization step is 100° C. or more. Since such a high temperature can be used in the present technology, short-time sterilization becomes possible. The heat sterilization temperature in the sterilization step is preferably 105° C. or more, more preferably 110° C. or more, even more preferably 112° C. or more, 114° C. or more, 116° C. or more or 118° C. or more, and particularly preferably 120° C. or more. By employing such a high temperature according to the present technology, it is possible to sterilize hard-to-kill bacteria in a short time. For example, according to the present technology, the heating conditions required for the sterilization of a retort food (120° C., 4 minutes or more) or the UHT method can be applied to lactoferrin.

The heat sterilization temperature in the sterilization step is preferably 180° C. or less, more preferably 160° C. or less, even more preferably 155° C. or less or 150° C. or less, and particularly preferably 140° C. or less. Too high a temperature may cause evaporation of water, resulting in a decrease in the amount of the resulting lactoferrin-containing aqueous solution.

According to a preferred embodiment of the present technology, the salt concentration of a lactoferrin-containing aqueous solution to be subjected to the sterilization step is 5 mM or less. Due to such a salt concentration, the formation of a precipitate is less likely to occur and the activity of lactoferrin is better maintained. The salt concentration of a lactoferrin-containing aqueous solution to be subjected to the sterilization step may preferably be 4 mM or less, more preferably 3 mM or less, and even more preferably 2 mM or less.

The salt concentration of a lactoferrin-containing aqueous solution to be subjected to the sterilization step may be, for example, more than 0 µM, 0.1 µM or more or more than 0.1 µM, 0.5 µM or more, 1 µM or more, 1.5 µM or more, or 10 µM or more from the viewpoint of the production efficiency of the aqueous solution.

The salt concentration of a lactoferrin-containing aqueous solution to be subjected to the sterilization step can be measured with an ICP-MS (inductively coupled plasma mass spectrometer).

The lactoferrin concentration of a lactoferrin-containing aqueous solution to be subjected to the sterilization step may preferably be 400 mg/ml or less, more preferably 200 mg/ml or less or 100 mg/ml or less, even more preferably 30 mg/ml or less, still more preferably 10 mg/ml or less, and particularly preferably 1 mg/ml or less. If the lactoferrin concentration is too high, lactoferrin may not be fully dissolved in the aqueous solution.

The lactoferrin concentration of a lactoferrin-containing aqueous solution to be subjected to the sterilization step may be at any low level as long as it is more than 0 mg/ml. The lactoferrin concentration of a lactoferrin-containing aqueous solution to be subjected to the sterilization step may be, for example, 0.00001 mg/ml or more, 0.0001 mg/ml or more, 0.001 mg/ml or more, or 0.01 mg/ml or more.

The heat sterilization time in the sterilization step may be set by one skilled in the art depending on factors such as sterilization temperature and sterilization method. The heat sterilization time in the sterilization step may be, for example, 0.5 seconds to 15 minutes, preferably 1 second to 10 minutes, and more preferably 1 second to 8 minutes.

In the case of using the UHT sterilization method, the heat sterilization time in the sterilization step is preferably 0.5 seconds to 10 seconds, more preferably 0.8 seconds to 8 seconds, and even more preferably 1 second to 5 seconds.

In the case of using a retort sterilization method, the heat sterilization time in the sterilization step is preferably 2 minutes to 10 minutes, more preferably 3 minutes to 8 minutes, and particularly 4 minutes to 7 minutes.

In the present technology, the heat sterilization time in the sterilization step refers to a period of time during which the temperature of a central portion of a lactoferrin-containing aqueous solution is maintained at a to-be-reached temperature (sterilization temperature) during the sterilization step.

In a particularly preferred embodiment of the present technology, the heat sterilization temperature and time in the sterilization step are 120° C. or more and 4 minutes or more, respectively. Such sterilization temperature and time satisfy the sterilization conditions required for retort sterilization.

A lactoferrin-containing aqueous solution to be subjected to the sterilization step preferably does not contain a stabilizer. The stabilizer refers to a component which is added, separately from a lactoferrin material used to prepare the lactoferrin-containing aqueous solution, to enhance the heat resistance of lactoferrin. The present technology makes it possible to maintain the activity of lactoferrin without using such a stabilizer, and to prevent the formation of a precipitate upon heating. Further, the absence of such a stabilizer can prevent a change in the flavor and/or the physical properties of the lactoferrin-containing aqueous solution produced.

The stabilizer can be exemplified by the stabilizers described in the above-listed patent literatures 3 and 4. Thus, a lactoferrin-containing aqueous solution to be subjected to the sterilization step does not contain one or more stabilizers such as a glycerin fatty acid ester, casein sodium, lecithin, a soybean polysaccharide, xanthane gum, pectin, gum arabic, ghatti gum, carrageenan, locust bean gum, and carboxymethyl cellulose. In particular, a lactoferrin-containing aqueous solution to be subjected to the sterilization step does not contain as a stabilizer any of a glycerin fatty acid ester, casein sodium, lecithin, a soybean polysaccharide, xanthane gum, pectin, gum arabic, ghatti gum, carrageenan, locust bean gum, and carboxymethyl cellulose.

A lactoferrin material for use in the preparation of a lactoferrin-containing aqueous solution to be subjected to the sterilization step sometimes contains casein sodium though in a very small amount. A lactoferrin material for use in the preparation of a lactoferrin-containing aqueous solution to be subjected to the sterilization step sometimes contains casein sodium in an amount of, for example, 5% by mass or less, particularly 2% by mass or less, and more particularly 0.5% by mass or less based on the mass of the lactoferrin material. The casein sodium, which is originally contained in the lactoferrin material, does not correspond to the above-described stabilizer.

The casein sodium concentration of a lactoferrin-containing aqueous solution to be subjected to the sterilization step may be, for example, 20 mg/ml or less, more preferably 10 mg/ml or less or 5 mg/ml or less, even more preferably 1.5 mg/ml or less, still more preferably 0.5 mg/ml or less, and particularly preferably 0.05 mg/ml or less. Particularly preferably, a lactoferrin-containing aqueous solution to be subjected to the sterilization step does not contain casein sodium.

In the production method of the present technology, the activity that lactoferrin had before the sterilization step is maintained after the sterilization step.

The antibacterial activity and/or the catechol-O-methyltransferase (hereinafter also referred to as COMT) inhibitory activity of lactoferrin, for example, may be used as an index of the maintenance of the activity of lactoferrin.

In the present technology, the maintenance of the activity may mean that a particular activity that lactoferrin had before the sterilization step is maintained, for example, at a level of 50% or more, preferably at a level of 60% or more, more preferably at a level of 70% or more, and even more preferably at a level of 80% or more after the sterilization step. In the present technology, the maintenance of the activity may mean that an activity that lactoferrin had before the sterilization step is maintained, for example, at a level of 90% or more after the sterilization step.

In the production method of the present technology, the activity that lactoferrin had before the sterilization step may be enhanced after the sterilization step. For example, the COMT inhibitory activity and the antibacterial activity of lactoferrin, especially the antibacterial activity of lactoferrin can be enhanced by the sterilization step in the production method of the present technology.

Thus, in the production method of the present technology, the activity that lactoferrin had before the sterilization step may be either maintained or enhanced after the sterilization step.

According to the present technology, the COMT inhibitory activity of lactoferrin in a lactoferrin-containing aqueous solution to be subjected to the sterilization step is preferably maintained, for example, at a level of 50% or more, preferably at a level of 60% or more, more preferably at a level of 70% or more, and even more preferably at a level of 80% or more after the sterilization step. Thus, the sterilization step of the present technology may be performed in such a manner that the COMT inhibitory activity of lactoferrin before the sterilization step is preferably maintained, for example, at a level of 50% or more, preferably at a level of 60% or more, more preferably at a level of 70% or more, and even more preferably at a level of 80% or more after the sterilization step.

COMT is expressed in various organs, and has a high activity in the liver and the kidney. COMT is also expressed in the intestine, particularly in the intestinal mucosa. The physiological role of COMT in the metabolism of a neurotransmitter has attracted attention in the field of pharmaceuticals.

In the present technology, the COMT inhibitory activity may be measured by a method described in Ikeda et al., Inhibitory Effect of Bovine Lactoferrin on Catechol-O-Methyltransferase, Molecules, 2017, 22, 1373. The details of the COMT inhibitory activity measuring method are described in the Test Examples below.

According to the present technology, the antibacterial activity of lactoferrin in a lactoferrin-containing aqueous solution to be subjected to the sterilization step is preferably maintained or enhanced after the sterilization step. The maintenance of the antibacterial activity may mean that the lactoferrin-containing aqueous solution inhibits the growth of bacteria, such as *Escherichia coli*, equally before and after the sterilization step. The enhancement of the antibacterial activity may mean that the lactoferrin-containing aqueous solution after the sterilization step inhibits the growth of bacteria, such as *Escherichia coli*, more than the lactoferrin-containing aqueous solution before the sterilization step.

According to a preferred embodiment of the present technology, in a lactoferrin-containing aqueous solution to be subjected to the sterilization step, the total content of proteins may preferably be 420 mg/ml or less, more preferably 31.5 mg/ml or less or 10.5 mg/ml or less, even preferably 1.05 mg/ml or less, and particularly preferably 0.2 mg/ml or less based on the mass of the aqueous solution. The use of a protein content that lies in such a range can better prevent the formation of a protein precipitate.

According to a preferred embodiment of the present technology, in a lactoferrin-containing aqueous solution to be subjected to the sterilization step, the amount of water may be, for example, 95% by mass or more, preferably 96% by mass or more, more preferably 97% by mass or more, even more preferably 98% by mass or more, still more preferably 99% by mass or more, and particularly preferably 99.5% by mass or more based on the mass of the aqueous solution. Thus, in a lactoferrin-containing aqueous solution to be subjected to the sterilization step, the amount of the components other than water may be, for example, 5% by mass or less, preferably 4% by mass or less, and more preferably 3% by mass or less based on the mass of the aqueous solution. Due to such a water content, the formation of a lactoferrin precipitate is less likely to occur.

In the present technology, the water is preferably pure water such as deionized water or Milli-Q water. The use of pure water can easily adjust the salt concentration.

According to a preferred embodiment of the present technology, in a lactoferrin-containing aqueous solution to be subjected to the sterilization step, the solid content concentration may be, for example, 45 w/v % or less, particularly 3 w/v % or less, and more particularly 0.1 w/v % or less.

According to a preferred embodiment of the present technology, the viscosity of a lactoferrin-containing aqueous solution to be subjected to the sterilization step may be, for example, 800 mPa·s or less, particularly 300 mPa·s or less, and more particularly 7 mPa·s or less at 25° C.

A method for heat-sterilizing a lactoferrin-containing aqueous solution in the sterilization step may be appropriately selected by one skilled in the art. For example, the UHT method or retort sterilization can be employed as a heat sterilization method. An apparatus for heat sterilization may be appropriately selected by one skilled in the art depending on the heat sterilization method employed. In the case of the UHT method, for example, heat sterilization can be performed by using a plate sterilizer. In the case of retort sterilization, heat sterilization can be performed by filling a lactoferrin-containing aqueous solution into a retort container, and then carrying out retort sterilization by using a retort sterilizer.

Usable heat sterilization methods are not limited to these methods. The sterilization step according to the present technology may be performed, for example, according to Production (Sterilization) Standard for Soft Drinks, the Food Sanitation Act, Ministry of Health, Labor and Welfare, Notice No. 213 (1986).

(2) Preparation Step

The production method according to the present technology may include a preparation step for preparing a lactoferrin-containing aqueous solution to be subjected to the sterilization step. The preparation step includes a step of mixing, for example, a lactoferrin material, an aqueous medium (e.g. water or an aqueous solution), and an optional other component(s). Lactoferrin contained in the lactoferrin material is dissolved in the water or aqueous medium.

In the preparation step, a lactoferrin-containing aqueous solution may be prepared in such a manner that the total mass content of proteins other than lactoferrin is 1/12 or less, preferably 1/14 or less, more preferably 1/16 or less, even more preferably 1/18 or less, and particularly preferably 1/20 or less of the mass content of lactoferrin. In order to prepare the lactoferrin-containing aqueous solution, a lactoferrin material of high lactoferrin purity may be dissolved in water or an aqueous solution. A lactoferrin material having a lactoferrin purity of, for example, 90% by mass or more, preferably 92% by mass or more, more preferably 94% by mass or more, even more preferably 95% by mass or more, and particularly preferably 96% by mass or more, may be used as the lactoferrin material.

In the preparation step, a lactoferrin-containing aqueous solution may be prepared in such a manner that the salt concentration of the lactoferrin-containing aqueous solution is preferably 5 mM or less, more preferably 4 mM or less, even more preferably 3 mM or less, and particularly preferably 2 mM or less. Such a salt concentration can be achieved by using a lactoferrin material having a low salt content.

A lactoferrin material having a high lactoferrin purity and a low salt content can be produced, for example, by subjecting lactoferrin-containing skim milk or whey to cation exchange resin adsorption treatment and ultrafiltration treatment. For example, lactoferrin is adsorbed onto a cation exchange resin by bringing skim milk or whey into contact with the cation exchange resin. The lactoferrin that has been adsorbed onto the cation exchange resin is separated from the cation exchange resin with salt water. Next, the lactoferrin is desalted using an ultrafiltration membrane to obtain a lactoferrin material having a high lactoferrin purity and a low salt content.

An ion exchanger for use in the cation exchange resin adsorption treatment preferably has a carboxymethyl (CM) group as an ion-exchanger functional group. The ion exchanger having a CM group as a functional group is exemplified by, but not limited to, CM-Sepharose FF (GE Healthcare Japan Corporation).

The concentration of salt water which is used to separate lactoferrin, which has been adsorbed onto the cation exchange resin, from the resin may be, for example, 5 to 15% by mass, preferably 6 to 14% by mass, and more preferably 8 to 12% by mass.

The molecular weight cut off of the ultrafiltration membrane may be, for example, 5,000 to 50,000, preferably 10,000 to 30,000, and more preferably 15,000 to 25,000. The ultrafiltration membrane is exemplified by, but not limited to, GR 61PP (manufacture by Alfa Laval, molecular weight cut off 20,000).

Preferably, in the preparation of a lactoferrin-containing aqueous solution to be subjected to the sterilization step, a proteinaceous material other than the lactoferrin material is not used. In the present technology, a proteinaceous material includes protein and peptide, particularly means only protein and peptide. By not using such a proteinaceous material in the preparation of the lactoferrin-containing aqueous solution, the content of contaminating protein in the lactoferrin-containing aqueous solution can be easily adjusted. Further, the formation of a precipitate in the sterilization step can be better prevented and the activity of lactoferrin can be better maintained and/or enhanced.

Examples of the optional other component may include a flavor, a colorant, a sweetener, an acidulant, and fruit juice. By preparing a lactoferrin-containing aqueous solution containing the optional other component in the preparation step, the lactoferrin-containing aqueous solution after the sterilization step can be used as it is as a beverage (e.g. a soft drink). The optional other component is preferably not a protein material.

The flavor can be exemplified by a fruit flavor (e.g. a strawberry flavor, a banana flavor, or a peach flavor), a coffee flavor, and a tea flavor.

The colorant can be exemplified by a natural colorant and a synthetic colorant.

The sweetener can be exemplified by a natural sweetener such as glucose, fructose or sucrose, and a high intensity sweetener such as aspartame, acesulfame potassium or sucralose.

The acidulant can be exemplified by citric acid, sodium citrate, malic acid, and tartaric acid.

The fruit juice can be exemplified by strawberry juice, banana juice, and peach juice.

(3) Filling Step

The production method according to the present technology may include a pre-sterilization filling step of filling a lactoferrin-containing aqueous solution to be subjected to the sterilization step into a container, or a post-sterilization filling step of filling a lactoferrin-containing aqueous solution after the sterilization step into a container. A filling method for use in such a filling step may be appropriately selected by one skilled in the art.

For example, in the pre-sterilization filling step, a lactoferrin-containing aqueous solution to be subjected to the sterilization step is filled into a retort pouch, and retort sterilization is performed in the sterilization step. In this manner, an aqueous lactoferrin solution, filled in the retort pouch and which is capable of long-term storage, can be produced.

Alternatively, for example, in the post-sterilization filling step, a lactoferrin-containing aqueous solution after the sterilization step may be aseptically filled into a container. In this manner, an aqueous lactoferrin solution, filled in the container and which is capable of long-term storage, can be produced.

As described hereinabove, the production method according to the present technology can provide a sterilized lactoferrin-containing aqueous solution filled in a container. The thus-produced aqueous lactoferrin solution may be provided to consumers or food/beverage manufacturers as a beverage or a material for foods and beverages in which the activity of lactoferrin has been maintained and which has an increased lactoferrin content.

The thus-produced aqueous lactoferrin solution, which has been heat-sterilized, is capable of long-term storage. For example, the aqueous lactoferrin solution product can be stored, for example for 3 months or more, preferably for 4 months or more, and more preferably for 5 months or more. The upper limit of the storage period may be, for example, 24 months or less, preferably 12 months or less, more preferably 10 months or less, and even more preferably 9 months or less.

2. Lactoferrin-Containing Aqueous Solution

The present technology provides a lactoferrin-containing aqueous solution in which the total mass content of proteins other than lactoferrin is 1/12 or less of the mass content of lactoferrin, and which does not contain living bacteria. The lactoferrin-containing aqueous solution containing no living bacteria can be distributed as it is as a beverage or can be used as a material for foods and beverages which does not require heat sterilization.

In the present technology, the presence or absence of living bacteria in a lactoferrin-containing aqueous solution may be determined by the presence or absence of living *Clostridium botulinum*. The presence or absence of living *Clostridium botulinum* may be determined by a method according to the procedure described in "Guidelines on food hygiene inspection of microorganisms", 2004, Japan Food Hygiene Association.

Preferably, in a lactoferrin-containing aqueous solution according to the present technology, the total mass content of proteins other than lactoferrin is 1/12 or less, preferably 1/14 or less, more preferably 1/16 or less, even more preferably 1/18 or less, and particularly preferably 1/20 or less of the mass content of lactoferrin. This reduces the formation of a precipitate in the aqueous solution.

In a lactoferrin-containing aqueous solution according to the present technology, the lower limit of the total mass content of proteins other than lactoferrin may be, for example, 0% by mass or, from the viewpoint of the production efficiency, may be more than 0% by mass. Thus, in a lactoferrin-containing aqueous solution according to the present technology, the total mass content of proteins other than lactoferrin may be, for example, 1/100,000 or more, 1/10,000 or more, 1/5,000 or more, 1/1,000 or more, or 1/100 or more.

The salt concentration of a lactoferrin-containing aqueous solution according to the present technology is preferably 5 mM or less, more preferably 4 mM or less, even more preferably 3 mM or less, and particularly preferably 2 mM or less. This reduces the formation of a precipitate in the aqueous solution.

The salt concentration of a lactoferrin-containing aqueous solution according to the present technology may be, for example, more than 0 μM, 0.1 μM or more, or more than 0.1 μM, 0.5 μM or more, 1 μM or more, 1.5 μM or more, or 10 μM or more from the viewpoint of the production efficiency of the aqueous solution.

The lactoferrin concentration of a lactoferrin-containing aqueous solution according to the present technology may preferably be 400 mg/ml or less, more preferably 200 mg/ml or less or 100 mg/ml or less, even more preferably 30 mg/ml or less, still more preferably 10 mg/ml or less, and particularly preferably 1 mg/ml or less.

The lactoferrin concentration of a lactoferrin-containing aqueous solution according to the present technology may be at any low level as long as it is more than 0 mg/ml. The lactoferrin concentration of a lactoferrin-containing aqueous solution to be subjected to the sterilization step may be, for example, 0.00001 mg/ml or more, 0.0001 mg/ml or more, 0.001 mg/ml or more, or 0.01 mg/ml or more.

A lactoferrin-containing aqueous solution according to the present technology preferably does not contain a stabilizer. A lactoferrin-containing aqueous solution according to the present technology does not contain one or more stabilizers such as a glycerin fatty acid ester, casein sodium, lecithin, a soybean polysaccharide, xanthane gum, pectin, gum arabic, ghatti gum, carrageenan, locust bean gum, and carboxymethyl cellulose. In particular, the lactoferrin-containing aqueous solution does not contain as a stabilizer any of a glycerin fatty acid ester, casein sodium, lecithin, a soybean polysaccharide, xanthane gum, pectin, gum arabic, ghatti gum, carrageenan, locust bean gum, and carboxymethyl cellulose.

A lactoferrin-containing aqueous solution according to the present technology preferably contains active lactoferrin. The active lactoferrin may be lactoferrin e.g. having a COMT inhibitory activity and/or an antibacterial activity. A lactoferrin-containing aqueous solution containing such active lactoferrin can be preferably obtained by the method described above under the heading "1. Method for Producing Lactoferrin-Containing Aqueous Solution".

A lactoferrin-containing aqueous solution according to the present technology may contain an optional other component(s) such as a flavor, a colorant, a sweetener, an acidulant, and fruit juice. The optional other component is as explained in "1. Method for Producing Lactoferrin-Containing Aqueous Solution".

The total content of proteins in a lactoferrin-containing aqueous solution according to the present technology may preferably be 420 mg/ml or less, more preferably 210 mg/ml or less or 105 mg/ml or less, even more preferably 31.5 mg/ml or less, still more preferably 10.5 mg/ml or less, and particularly preferably 1.05 mg/ml or less based on the mass of the aqueous solution. Because of this, the formation of a precipitate is less likely to occur.

The amount of water in a lactoferrin-containing aqueous solution according to the present technology may be, for example, 95% by mass or more, preferably 96% by mass or more, and more preferably 97% by mass or more based on the mass of the aqueous solution. Thus, in a lactoferrin-containing aqueous solution according to the present technology, the amount of the components other than water may be, for example, 5% by mass or less, preferably 4% by mass or less, and more preferably 3% by mass or less based on the mass of the aqueous solution.

According to a preferred embodiment of the present technology, in a lactoferrin-containing aqueous solution to be subjected to the sterilization step, the solid content concentration may be, for example, 45 w/v % or less, particularly 3 w/v % or less, and more particularly 0.1 w/v % or less.

According to a preferred embodiment of the present technology, the viscosity of a lactoferrin-containing aqueous solution to be subjected to the sterilization step may be, for example, 800 mPa·s or less, particularly 300 mPa·s or less, and more particularly 7 mPa·s or less at 25° C.

A lactoferrin-containing aqueous solution according to the present technology can be produced by the production method described above under the heading "1. Method for Producing Lactoferrin-Containing Aqueous Solution". The production method can maintain the activity of lactoferrin. Thus, the present technology can provide a lactoferrin-containing aqueous solution in which the activity of lactoferrin has been maintained and which does not contain living bacteria.

The present technology will be described in greater detail with reference to the following examples, but is not limited to the examples in any way.

EXAMPLES

Test Example 1

Lactoferrin (manufactured by Morinaga Milk Industry Co., Ltd., lactoferrin purity 96% by mass or more) was added to deionized water such that the final concentration became 30 mg/mL, thereby preparing a lactoferrin-containing aqueous solution. The lactoferrin is a lactoferrin material produced by the procedure described in Example 3 below. Alpha-casein, bovine serum albumin (BSA), alpha-lactalbumin (αLA) and casein sodium (casein Na) were provided as additional proteins to be added to the lactoferrin-containing aqueous solution. One of the additional proteins was mixed into the lactoferrin-containing aqueous solution such that the final concentration of the additional protein became 0.3 mg/mL, 0.6 mg/mL, 1.2 mg/mL, or 2.4 mg/mL. In this manner, four samples were obtained for each additional protein. From the above lactoferrin purity and the additional protein concentrations, the ratio of the total mass content of proteins other than lactoferrin to the mass content of lactoferrin (the total mass content of proteins other than lactoferrin/the mass content of lactoferrin) in the samples can be calculated to be 1/19 or less, 1/16 or less, 1/12 or less, and 1/8 or less for the concentration of each additional protein. A lactoferrin-containing aqueous solution, to which no additional protein had been added, was also provided as a sample. In the lactoferrin-containing aqueous solution containing no additional protein, the ratio of the total mass content of proteins other than lactoferrin to the mass content of lactoferrin was 1/24 or less.

The 17 samples thus obtained (four samples with varying additional protein concentrations for each of the four additional proteins and one sample containing no additional protein) were subjected to autoclave sterilization at 121° C. for 10 minutes. The turbidity of each sample after the autoclave sterilization was measured with a Hitachi spectrophotometer U-3900 (manufactured by Hitachi, Ltd.). The measurement wavelength was 660 nm. The results of the turbidity measurement are shown in Table 1 below and in FIG. 1.

TABLE 1

Results of Absorbance Measurement

| Additional protein conc. (mg/ml) | Alpha-casein | BSA | αLA | Casein Na |
|---|---|---|---|---|
| 0 | 0.032 | 0.032 | 0.032 | 0.032 |
| 0.3 | 0.049 | 0.044 | 0.045 | 0.057 |
| 0.6 | 0.067 | 0.056 | 0.046 | 0.07 |
| 1.2 | 0.099 | 0.094 | 0.054 | 0.11 |
| 2.4 | 0.169 | 0.175 | 0.103 | 0.183 |

As shown in Table 1 and FIG. 1, the addition of any of the additional proteins to the lactoferrin-containing aqueous solution caused an increase in the turbidity of the aqueous solution upon the heat treatment. The higher the concentration of an additional protein, the larger the increase in turbidity. Thus, the lower the mass content of proteins other than lactoferrin protein, the smaller the increase in turbidity upon the heat treatment of the lactoferrin-containing aqueous solution. It is therefore conceivable that the lower the mass content of proteins other than lactoferrin protein is, the less the formation of a protein precipitate is likely to occur upon the heating at 120° C. It is also conceivable that the less the formation of a protein precipitate is, the better the activity of lactoferrin is maintained.

As shown in Table 1 and FIG. 1, the turbidity after the heat treatment is about 0.1 or 0.1 or less when the concentration of an additional protein is 1.2 mg/mL or less, i.e. when the ratio of the total mass content of proteins other than lactoferrin to the mass content of lactoferrin is 1/12 or less. A change in the quality of a lactoferrin-containing aqueous solution before and after the heat treatment is preferably as small as possible; in particular, it is preferred that the turbidity of a lactoferrin-containing aqueous solution after the heat treatment is about 0.1 or less. For example, when the turbidity of a lactoferrin-containing aqueous solution is low even after the heat treatment, mixing of microorganisms into the aqueous solution product or a change in the product (the formation of a precipitate or an increase in the turbidity) can be easily checked apparently in quality control of the product. When the ratio of the total mass content of proteins other than lactoferrin to the mass content of lactoferrin is 1/12 or less, the lactoferrin-containing aqueous solution is maintained in a desirable state, in particular, no formation of a precipitate occurs, even when the solution is heat-sterilized at 120° C. Further, it is conceivable that the activity of lactoferrin is well maintained when the ratio of the total mass content of proteins other than lactoferrin to the mass content of lactoferrin is 1/12 or less.

The turbidity of the lactoferrin-containing aqueous solution after the heat treatment was 0.032 when the solution contained no additional protein material other than the lactoferrin material, i.e. when the ratio of the total mass content of proteins other than lactoferrin to the mass content of lactoferrin was 1/24 or less. This indicates that a particularly preferable lactoferrin-containing aqueous solution can be obtained in such a case.

Test Example 2

Lactoferrin (manufactured by Morinaga Milk Industry Co., Ltd., lactoferrin purity 96% by mass or more) was added to deionized water such that the final concentration became 30 mg/mL, thereby preparing a lactoferrin-containing aqueous solution. NaCl, $CaCl_2$ or $MgCl_2$ was mixed into the lactoferrin-containing aqueous solution. Of these salts, NaCl and $CaCl_2$ were each added such that its final concentration became 1.25 mM, 2.5 mM, 5 mM, 10 mM, 15.6 mM, or 20 mM. Thus, six samples having the varying salt concentrations were obtained for each salt. On the other hand, $MgCl_2$ was added such that its final concentration became 1.25 mM, 2.5 mM, 5 mM, 7.6 mM, 10 mM, or 20 mM. Thus, six samples having the varying salt concentrations were obtained.

A total of 18 samples thus obtained (six samples with varying salt concentrations for each of the three salts) were subjected to autoclave sterilization at 121° C. for 10 minutes. The turbidity of each sample after the autoclave sterilization was measured. The measurement wavelength was 660 nm. The results of the turbidity measurement are shown in Table 2 below and in FIG. 2.

TABLE 2

Results of Absorbance Measurement

| Salt conc. (mM) | NaCl | $CaCl_2$ | $MgCl_2$ |
|---|---|---|---|
| 20 | 0.823 | 3.2 | 3.32 |
| 15.6 | 0.322 | 2.06 | — |
| 10 | 0.095 | 0.263 | 0.357 |
| 7.6 | — | — | 0.162 |
| 5 | 0.05 | 0.073 | 0.073 |
| 2.5 | 0.041 | 0.048 | 0.047 |
| 1.25 | 0.037 | 0.045 | 0.04 |

Figure 2:
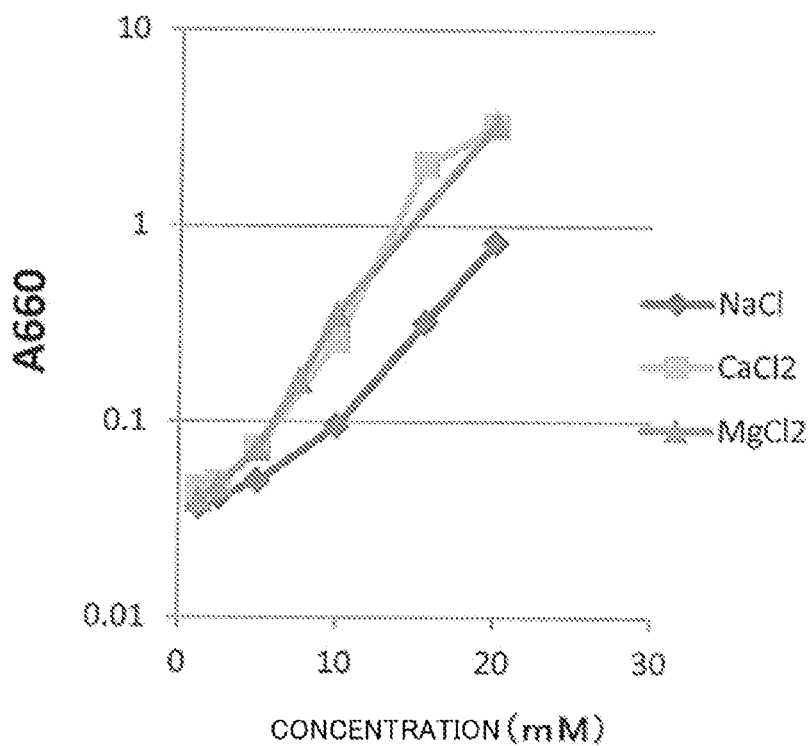
FIG. 2 is a graph showing the results of measurement of the turbidities of lactoferrin-containing aqueous solutions after autoclave sterilization.

As can be seen in Table 2 and FIG. 2, the addition of any of the salts to a lactoferrin-containing aqueous solution causes an increase in the turbidity of the aqueous solution upon the heat treatment. The higher the concentration of a salt, the larger the increase in turbidity. Thus, the lower the salt concentration, the smaller the increase in turbidity upon the heat treatment of the lactoferrin-containing aqueous solution. It is therefore conceivable that the lower the salt concentration is, the less the formation of a protein precipitate is likely to occur.

It is desirable for a lactoferrin-containing aqueous solution if the turbidity after the heat treatment is about 0.1 or less. As can be seen in Table 2 and FIG. 2, the turbidity after the heat treatment is less than 0.1 when the salt concentration is 5 mM or less. Thus, when the salt concentration of a lactoferrin-containing aqueous solution is 5 mM or less, the aqueous solution is maintained in a desirable state, in particular, no formation of a precipitate occurs, even when the aqueous solution is heat-sterilized at 120° C.

The data in Table 2 and FIG. 2 indicates that the turbidity decreases with a decrease in the salt concentration. It is therefore conceivable that if the same test is conducted on a sample to which no salt is added, then the turbidity will be lower than that of a sample having a salt concentration of 1.25 mM.

Test Example 3

The following test was conducted to demonstrate that the use of different lactoferrin materials produces a difference in the turbidity between the resulting lactoferrin-containing aqueous solutions. Two types of lactoferrin materials were provided (material 1 manufactured by Tatua, material 2 manufactured by Fonterra). Each of the lactoferrin materials was added to Milli-Q water such that the final concentration became 30 mg/mL, thereby preparing a lactoferrin-containing aqueous solution. In this manner, two types of lactoferrin-containing aqueous solutions were prepared (the solution of material 1 will be referred to as sample 1, and the solution of material 2 will be referred to as sample 2). Each of sample 1 and sample 2 was subjected to autoclave sterilization at 121° C. for 10 minutes. The turbidity of each sample after the autoclave sterilization was measured. The measurement wavelength was 660 nm. The results of the turbidity measurement are shown in Table 3 below and in FIG. 3.

TABLE 3

Results of Absorbance Measurement

|  | Sample 1 | Sample 2 |
|---|---|---|
| Heat-treated | 0.119 | 0.038 |
| Non-heat-treated | 0.037 | 0.031 |

Figure 3:
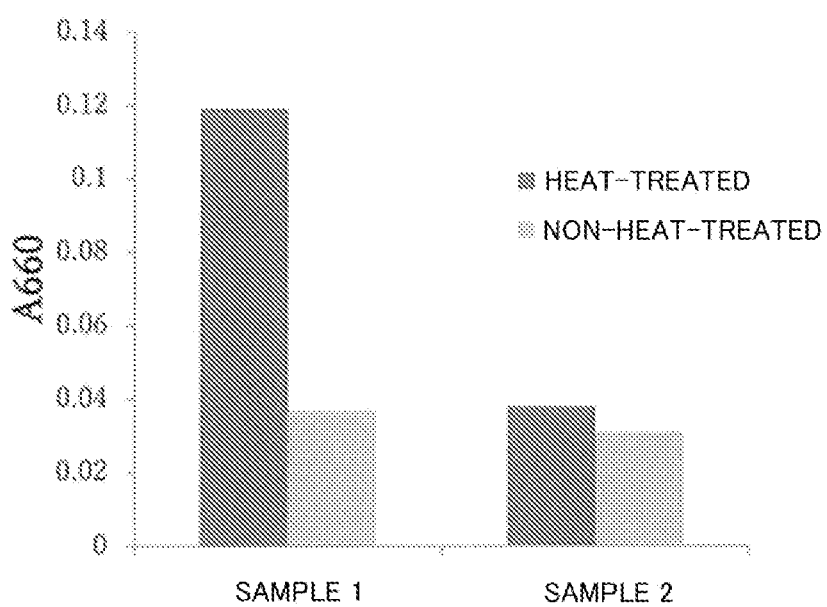
FIG. 3 is a graph showing the results of measurement of the turbidities of lactoferrin-containing aqueous solutions after autoclave sterilization.

As will be appreciated from the data in Table 3 and FIG. 3, some types of lactoferrin materials undergo an increase in the turbidity by the heat treatment.

Test Example 4

The following test was conducted to determine a relationship between an increase in the turbidity of an aqueous lactoferrin solution by heat treatment and the COMT inhibitory activity.

Lactoferrin (manufactured by Morinaga Milk Industry Co., Ltd., lactoferrin purity 96% by mass or more) was added to deionized water such that the final concentration became 30 mg/mL, thereby preparing a lactoferrin-containing aqueous solution. NaCl, albumin (BSA) or casein sodium was mixed into the lactoferrin-containing aqueous solution. NaCl was added such that its concentration became 0 mM, 10 mM, 15 mM, or 20 mM. BSA or casein sodium was added such that its concentration became 0 mg/mL, 0.6 mg/mL, 2.4 mg/mL, or 4.8 mg/mL.

A total of 12 solutions thus prepared were subjected to autoclave sterilization at 121° C. for 10 minutes. The turbidity of each sample after the autoclave sterilization was measured. The measurement wavelength was 660 nm.

Further, each solution after the autoclave sterilization was subjected to centrifugal treatment at 150,000×g for 20 minutes, and the COMT inhibitory activity of the supernatant was measured. The measurement of the COMT inhibitory activity was performed in the following manner: 22.5-μL reaction liquids, each including 50 mM of phosphoric acid (pH 7.8), 2 mM of $MgCl_2$, 11.2 μM of SAM (S-adenosyl-L-methionine) labeled with $^{14}C$ radioisotope, 1 mM of DTT (dithiothreitol), 4 μg/mL of COMT enzyme and each of the above solutions, were prepared. Each of the solutions had been diluted to a concentration of 0.1 mg/mL, and heat-treated at 100° C. for 10 minutes prior to a reaction. An enzymatic reaction was carried out by allowing each reaction liquid to react at 37° C. for 10 minutes, then adding 2.5 μL of DBA (dihydroxy benzoic acid) as a substrate to the reaction liquid, and then allowing the reaction liquid to react at 37° C. for 10 minutes. The reaction was terminated by adding 12.5 μL of 1M HCl to the reaction liquid. After the termination of the reaction, 300 μL of an isoamyl alcohol/toluene (3:7) solution was added to the reaction liquid to carry out extraction, and the amount of radiation was counted with a liquid scintillation counter.

Figure 4:
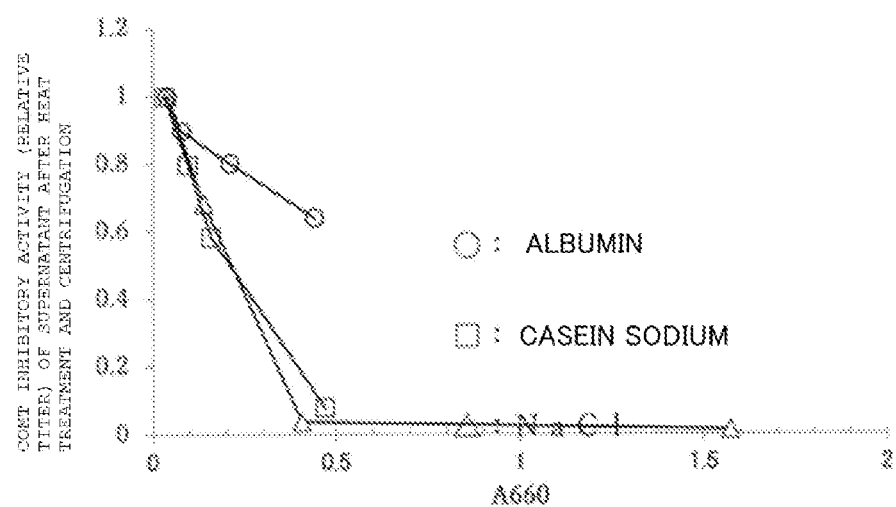
FIG. 4 is a graph showing a relationship between the COMT inhibitory activity and the turbidity of a lactoferrin-containing aqueous solution.

Next, for each of the 12 solutions, the amount of the solution necessary for 50% inhibition of the COMT activity was calculated. When the amount of the solution solely containing lactoferrin, necessary for 50% inhibition of the COMT activity, is assumed to be 1, then the amount of a lactoferrin-containing aqueous solution also containing the salt or protein, necessary for 50% inhibition of the COMT activity, should be higher than 1 because of lower COMT inhibitory, activity of the solution. The COMT inhibitory activity (relative titer) of the supernatant of each solution was calculated according to the following calculation formula: "Relative Titer"="amount of autoclave-sterilized solution solely containing lactoferrin, necessary for 50% inhibition of the COMT activity"/"amount of autoclave-sterilized solution also containing the salt or protein, necessary for 50% inhibition of the COMT activity". Table 4 and FIG. 4 show a relationship between the calculated relative titer and the turbidity after autoclave sterilization for each sample.

TABLE 4

Relationship between Turbidity and COMT inhibitory Activity

NaCl

| Concentration (mM) | Turbidity | COMT inhibitory activity |
|---|---|---|
| 0 | 0.04 | 1.000 |
| 10 | 0.14 | 0.683 |
| 15 | 0.407 | 0.037 |
| 20 | 1.574 | 0.012 |

| Concentration (mg/ml) | Turbidity | COMT inhibitory activity |
|---|---|---|
| BSA | | |
| 0 | 0.04 | 1.000 |
| 0.6 | 0.079 | 0.898 |
| 2.4 | 0.211 | 0.802 |
| 4.8 | 0.441 | 0.640 |
| Casein Na | | |
| 0 | 0.032 | 1.000 |
| 0.6 | 0.097 | 0.797 |
| 2.4 | 0.16 | 0.583 |
| 4.8 | 0.47 | 0.079 |

As can be seen in Table 4 and FIG. 4, the COMT inhibitory activity of the supernatant of each solution after centrifugal treatment decreases with increase in the turbidity. Thus, there appears to be a correlation between the turbidity and the COMT inhibitory activity. It is therefore conceivable that the activity of lactoferrin is maintained when the formation of a precipitate is prevented as observed in Test Examples 1 and 2.

As will be inferred from the results of Test Examples 1 and 2 as well as the results of Test Example 4, in order to maintain the COMT inhibitory activity of lactoferrin in a lactoferrin-containing aqueous solution at a level of about 80% of the COMT inhibitory activity before heat sterilization (i.e. at a COMT inhibitory activity ratio of about 0.8), it is particularly preferred to make the total mass content of proteins other than lactoferrin 1/20 or less of the mass content of lactoferrin, and to make the salt concentration 5 mM or less.

Test Example 5

Lactoferrin (manufactured by Morinaga Milk Industry Co., Ltd., lactoferrin purity 96% by mass or more) was dissolved in ion-exchanged water to obtain a lactoferrin-containing aqueous solution having a concentration of 1 mg/mL, 10 mg/mL or 30 mg/mL. Each of the resulting lactoferrin-containing aqueous solutions was subjected to retort heat treatment (121° C., 7 min), and stored at a temperature of 5° C., 25° C. or 37° C. for 44 days or 98 days. Thereafter, each lactoferrin-containing aqueous solution was added to a 0.08 vol % TFA (trifluoroacetic acid) solution such that the lactoferrin concentration became 0.1 mg/mL, thereby obtaining a sample for HPLC analysis. HPLC analysis was performed using each of the thus-obtained samples in an amount of 40 μL. In the HPLC analysis, using a Cosmosil 5C4-MS (4.6 mm×250 mm) column, elution was performed with a concentration gradient of acetonitrile containing 0.1 vol % TFA, and lactoferrin was detected at 280 nm. A lactoferrin detection rate (the percentage of the absorbance of a sample after the retort heat treatment relative to the absorbance of the sample before the retort heat treatment as 100%) was calculated for each sample. The thus-obtained detection rates are shown in Table 5 and FIG. 5.

TABLE 5

| | Lactoferrin Detection Rate (%) | | | | | | |
|---|---|---|---|---|---|---|---|
| Conc. | Before heating | 5° C. D 44 | 25° C. D 44 | 37° C. D 44 | 5° C. D 98 | 25° C. D 98 | 37° C. D 98 |
| 1 mg/ml | 100.0 | 97.5 | 107.4 | 104.5 | 110.4 | 107.9 | 103.6 |
| 10 mg/ml | 100.0 | 100.6 | 103.6 | 95.7 | 95.9 | 96.8 | 93.8 |
| 30 mg/ml | 100.0 | 97.5 | 103.4 | 95.4 | 102.2 | 101.2 | 99.5 |

Figure 5:
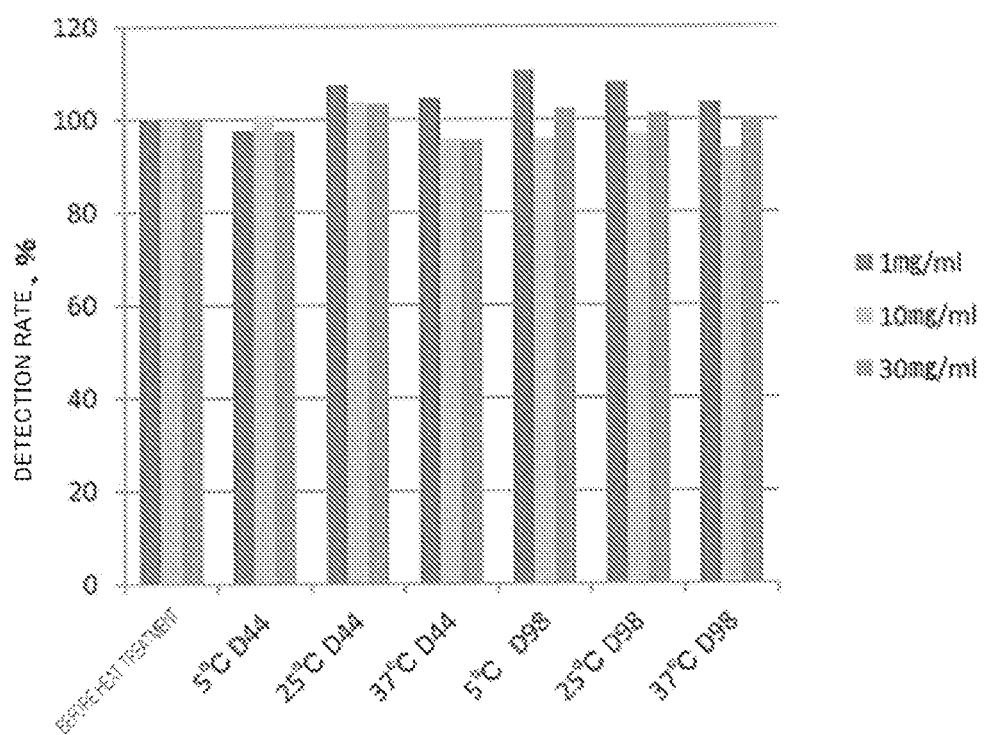
FIG. 5 is a graph showing the results of HPLC analysis of lactoferrin-containing aqueous solutions.

As can be seen in Table 5 and FIG. 5, the amounts of lactoferrin, detected by HPLC analysis, in the samples which had been stored over a long period of time after the retort heat treatment were nearly equal to those of the samples before the retort heat treatment. The data thus verifies that a lactoferrin-containing aqueous solution which has been sterilized according to the present technology undergoes little quality change even when it is stored over a long period of time.

Test Example 6

Lactoferrin (manufactured by Morinaga Milk Industry Co., Ltd., lactoferrin purity 96% by mass or more) was dissolved in deionized water such that the concentration became 10 mg/mL, thereby preparing a lactoferrin-containing aqueous solution. The aqueous solution was subjected to retort treatment at 121° C. for 7 minutes. After the retort treatment, the aqueous solution was stored at 5° C., 25° C. or 37° C. for 98 days. After the storage, the COMT inhibitory activities of the aqueous solutions that had been stored at the varying temperatures were measured. A count value for a radioactive substance was used as an index of the COMT inhibitory activity.

COMT inhibitory activity was measured also for a lactoferrin-containing aqueous solution which had not undergone retort treatment, and for a measurement sample to which no lactoferrin had been added.

Figure 6:
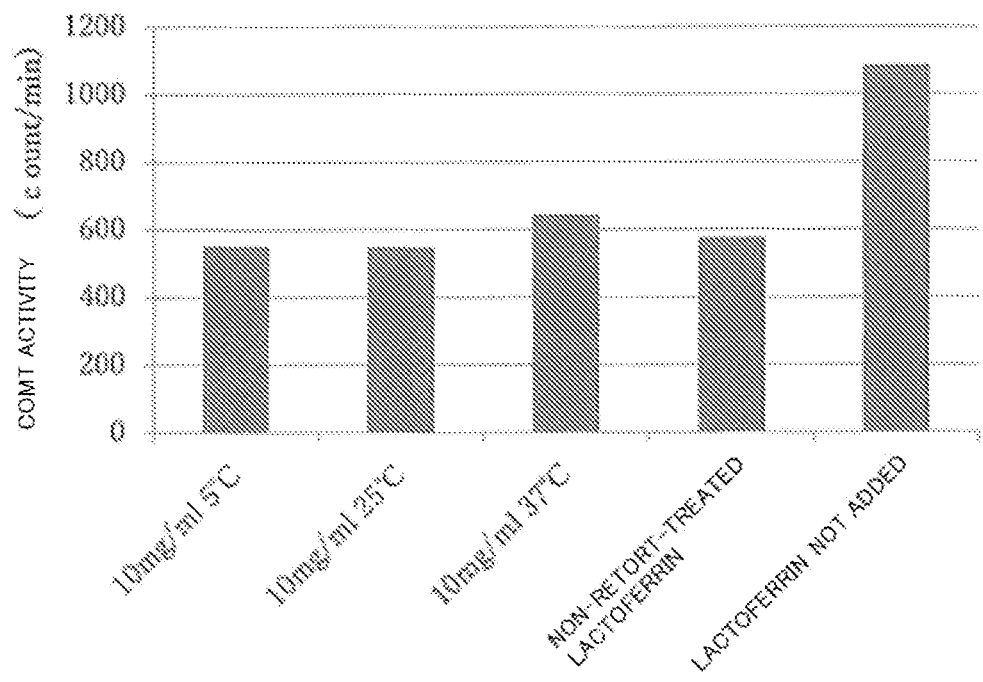
FIG. 6 is a graph showing the results of measurement of the COMT inhibitory activities of lactoferrin-containing aqueous solutions.

The results of the measurement are shown in Table 6 and FIG. 6.

TABLE 6

Results of Measurement of COMT inhibitory Activity

| Sample | COMT activity |
|---|---|
| 10 mg/mL 5° C. | 551 |
| 10 mg/mL 25° C. | 547.5 |
| 10 mg/mL 37° C. | 644 |

TABLE 6-continued

Results of Measurement of COMT inhibitory Activity

| Sample | COMT activity |
|---|---|
| Non-retort-treated lactoferrin | 576 |
| lactoferrin not added | 1085.5 |

As can be seen from comparison in Table 6 and FIG. 6 between the data for the lactoferrin-containing aqueous solution which had not undergone retort treatment and the data for the measurement sample containing no lactoferrin, lactoferrin inhibits COMT. Further, as can be seen from comparison between the data for the lactoferrin-containing aqueous solution which had not undergone the retort treatment and the data for the three lactoferrin-containing aqueous solutions which had undergone the retort treatment, any of the latter three aqueous solutions after the retort treatment has a COMT inhibitory activity comparable to that of the former aqueous solution which had not undergone the retort treatment. This verifies that a lactoferrin-containing aqueous solution, produced according to the present technology, maintains its COMT inhibitory activity even though it has undergone the sterilization step.

Test Example 7

Lactoferrin (manufactured by Morinaga Milk Industry Co., Ltd., lactoferrin purity 96% by mass or more) was dissolved in deionized water such that the concentration became 30 mg/mL, thereby obtaining a lactoferrin-containing aqueous solution. The lactoferrin-containing aqueous solution was subjected to autoclave treatment at 121° C. for 10 minutes, and the antibacterial activity of the solution was checked as follows. *Escherichia coli* were incubated in 5-mL M9 broth, and the bacterial cells were centrifugally recovered. The recovered bacterial cells were suspended in PBS (phosphate buffered saline, pH 7.4), and two 100-µL suspensions having an OD of 0.2 (630 nm) were prepared. On the other hand, PBS was added to the above lactoferrin-containing aqueous solution such that the lactoferrin concentration became 2 mg/ml, thereby obtaining a diluted lactoferrin-containing aqueous solution. The diluted lactoferrin-containing aqueous solution was added to each of the two 100-µL suspensions in equal amount (100 µL), thereby preparing two liquids containing lactoferrin in a final concentration of 1 mg/mL and bacterial cells.

A lactoferrin-containing aqueous solution, which had not undergone the autoclave treatment, was added to two 100-µL suspensions which had been prepared in the above-described manner, thereby preparing two liquids containing lactoferrin in a final concentration of 1 mg/mL and bacterial cells.

Two 100-µL suspensions, to which a lactoferrin-containing aqueous solution had not been added, were also provided.

Each of the above six samples was incubated at 37° C. for 1 hour, and then the sample was subjected to centrifugation. A precipitate, obtained by the centrifugation, was suspended in PBS, and suspended matter was applied to an M9 plate. The plate was incubated overnight at 37° C. to form colonies, and the number of the colonies was measured. The average value of the measured numbers of colonies is shown in Table 7 and FIG. 7.

TABLE 7

Results of Measurement of Antibacterial Activity

| | Average value | SD |
|---|---|---|
| Lactoferrin not treated | 298.5 | 19.5 |
| Lactoferrin heat-treated | 144 | 18 |
| No lactoferrin | 364 | 11 |

Figure 7:
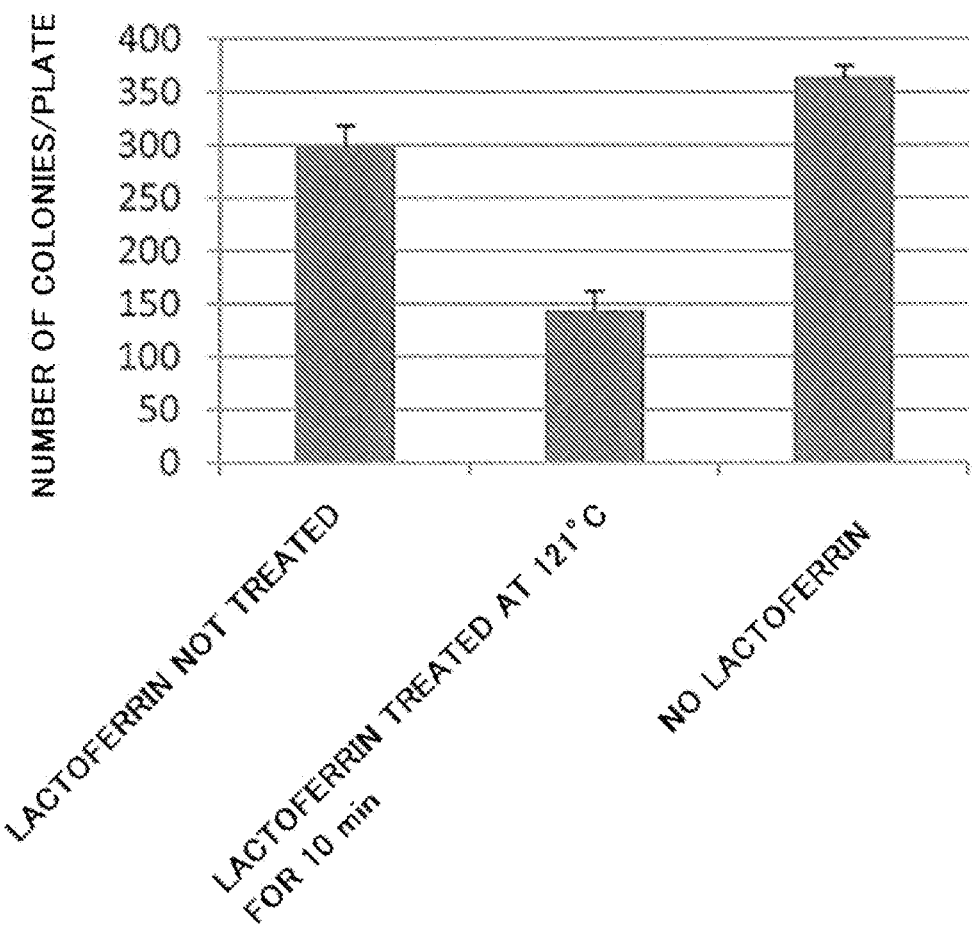
FIG. 7 is a graph showing the results of measurement of the antibacterial activities of lactoferrin-containing aqueous solutions.

As can be seen from comparison in Table 7 and FIG. 7 between the data for the samples containing no lactoferrin and the data for the samples containing the lactoferrin-containing aqueous solution which had not undergone the autoclave treatment, the lactoferrin-containing aqueous solution has an antibacterial activity. Further, as can be seen from comparison between the data for the samples containing the lactoferrin-containing aqueous solution which had not undergone the autoclave treatment and the data for the samples containing the lactoferrin-containing aqueous solution which had undergone the autoclave treatment, the antibacterial activity is enhanced by the autoclave treatment. This verifies that a lactoferrin-containing aqueous solution, produced according to the present technology, has an antibacterial activity which has been enhanced by the sterilization step.

Example 1

Lactoferrin (manufactured by Morinaga Milk Industry Co., Ltd., lactoferrin purity 96% by mass or more) was dissolved in deionized water such that the concentration became 10 mg/ml, and 0.1% (w/v) of a strawberry flavor (T. Hasegawa Co., Ltd.) and 0.02% (w/v) of a colorant (T. Hasegawa Co., Ltd.) were added to the solution, thereby obtaining a lactoferrin-containing aqueous solution. The resulting lactoferrin-containing aqueous solution was sterilized by heating at 131° C. for 30 seconds using a plate sterilizer (manufactured by Morinaga Engineering Co., Ltd.). After cooling the sterilized solution, it was aseptically filled into a container, thereby obtaining a lactoferrin-containing beverage capable of long-term storage.

Example 2

Lactoferrin (manufactured by Morinaga Milk Industry Co., Ltd., lactoferrin purity 96% by mass or more) and NaCl were dissolved in deionized water such that the concentration of lactoferrin became 30 mg/ml and the concentration of NaCl became 2 mM, thereby obtaining 10 L of a lactoferrin-containing aqueous solution. The resulting lactoferrin-containing aqueous solution was dispensed into a retort pouch. After the dispension, the retort pouch containing the aqueous solution was sterilized at 120° C. for minutes in a retort sterilizer, thereby obtaining a lactoferrin-containing aqueous solution capable of long-term storage.

Example 3

A lactoferrin material having a high lactoferrin purity and a low salt content was obtained in the following manner.

First, 1 L of an ion exchanger (CM-Sepharose FF (GE Healthcare Japan Corporation) was packed into a column, and 2 L of 0.1 N hydrochloric acid was passed through the column, followed by cleaning with water to equilibrate the ion exchanger. Subsequently, the ion exchanger was taken out of the column, and put into 100 L of bovine skim milk at a pH of 6.7 which had been cooled to 4° C., and the mixture was stirred at 4° C. for 6 hours. The skim milk was removed by filtration to collect the ion exchanger, and the ion exchanger was packed into a column. The column was cleaned with deionized water to remove the remaining skim milk. Thereafter, 5 L of 10% by mass salt water was passed through the column to isolate a component that had been adsorbed onto the ion exchanger, thereby obtaining 5 L of recovered liquid. The recovered liquid was subjected to ultrafiltration at a circulation flow rate of 8 L/min and an average pressure of 30 kg/cm$^2$ using an ultrafiltration membrane GR 61PP (manufacture by Alfa Laval) having a molecular weight cut off of 20,000. Desalting was further performed by adding deionized water and repeatedly performing ultrafiltration. The resulting solution was freeze-dried to obtain 3.5 g of powdery lactoferrin. In this manner, a lactoferrin material having a purity of 96% by mass or more and a sodium salt content of 70 mg per 100 g was obtained.

The invention claimed is:

1. A method for producing an aqueous solution comprising lactoferrin, comprising heat-sterilizing an aqueous solution comprising lactoferrin at a temperature of 100° C. or more, wherein said solution has a total amount of proteins other than the lactoferrin that is 1/12 or less of an amount of the lactoferrin, as measured by mass,
   wherein the aqueous solution comprising lactoferrin comprises:
   a) concentration of a salt that is 5 mM or less, and
   b) an ionic strength ("I") that does not satisfy:

$\log I < -3$;

wherein the salt is a sodium salt, a calcium salt, or a magnesium salt.

2. The method according to claim 1, wherein said solution has a lactoferrin concentration of 400 mg/ml or less.

3. The method according to claim 1, wherein the temperature during said heat-sterilizing is 120° C. or more.

4. The method according to claim 1, wherein the temperature during said heat-sterilizing is 120° C. or more for 4 minutes or more.

5. The method according to claim 1, wherein said solution does not contain a stabilizer.

6. The method according to claim 1, wherein said solution has a catechol-O-methyltransferase ("COMT") inhibitory activity of lactoferrin that is maintained at a level of 80% or more after said heat-sterilizing.

7. A method for producing an aqueous solution comprising lactoferrin,
   wherein said method comprises heat-sterilizing an aqueous solution comprising lactoferrin at a temperature of 100° C. or more,
   wherein proteins other than the lactoferrin are present in said aqueous solution 1/12 or less as compared to the lactoferrin, by mass,
   wherein the aqueous solution comprising the lactoferrin has a lactoferrin concentration of 30 mg/ml or less;
   wherein the aqueous solution comprising the lactoferrin comprises concentration of a salt that is 5 mM or less,
   wherein the salt is a sodium salt, a calcium salt, or a magnesium salt.

8. A method for producing an aqueous solution comprising lactoferrin,
   wherein said method comprises heat-sterilizing a lactoferrin-containing aqueous solution at a temperature of 100° C. or more,
   wherein proteins other than the lactoferrin are present in said aqueous solution 1/20 or less as compared to the lactoferrin, by mass,
   wherein the aqueous solution comprising the lactoferrin comprises concentration of a salt that is 5 mM or less,
   wherein the salt is a sodium salt, a calcium salt, or a magnesium salt.

* * * * *